United States Patent [19]
Kukla et al.

[11] Patent Number: 5,626,474
[45] Date of Patent: May 6, 1997

[54] IMPLANT TORQUE WRENCH

[76] Inventors: Thomas S. Kukla; Ali Nematollahi, both of 1307 N. Court St., McHenry, Ill. 60050

[21] Appl. No.: 495,360

[22] Filed: Jun. 28, 1995

[51] Int. Cl.$^6$ ............................................. A61C 3/00
[52] U.S. Cl. ........................... 433/141; 81/467; 81/146; 81/153
[58] Field of Search ............................... 433/114, 124, 433/130, 141, 146, 147, 153, 161, 162, 163, 173; 81/467, 473, 474, 471

[56] References Cited

U.S. PATENT DOCUMENTS

| | | | |
|---|---|---|---|
| 852,159 | 4/1907 | Bode | 433/147 X |
| 2,468,193 | 4/1949 | Goff | 81/473 X |
| 3,283,621 | 11/1966 | Faso | 81/467 |
| 3,852,884 | 12/1974 | Lazarus | 81/54 |
| 4,465,463 | 8/1984 | H:Son Olde | 433/141 |
| 4,480,997 | 11/1984 | Deutsch et al. | 433/221 |
| 4,976,617 | 12/1990 | Carchidi | 433/141 |
| 5,064,375 | 11/1991 | Jorneus | 433/229 |
| 5,098,293 | 3/1992 | Loof et al. | 433/165 |
| 5,129,823 | 7/1992 | Hughes | 433/141 |
| 5,158,458 | 10/1992 | Perry | 433/141 |
| 5,209,658 | 5/1993 | Brahler | 433/125 |
| 5,236,359 | 8/1993 | Myers et al. | 433/144 |
| 5,295,831 | 3/1994 | Patterson et al. | 433/141 |
| 5,347,894 | 9/1994 | Fischer | 81/471 |
| 5,437,524 | 8/1995 | Huang | 81/474 X |

*Primary Examiner*—Christopher A. Bennett
*Attorney, Agent, or Firm*—Charles F. Meroni, Jr.

[57] ABSTRACT

A manually operated dental implant torque wrench has an elongated shaft assembly having a first shaft end and a second shaft end. A manually operable control device is connected to the first shaft end of the elongated shaft assembly for rotating the elongated shaft assembly. An angled housing assembly having a passageway extending from a first open end of the housing to a second open end of the housing is provided. The housing having a first portion and a second portion in an angled relationship to the first portion. A drive assembly is provided within the passageway and is operatively connected to the elongated shaft assembly. The drive assembly includes a receptacle end rotatably mounted to the second open end and adapted for attaching a dental tool thereto. An adjustable torque limiting assembly is connected to the elongated shaft assembly for disengaging the elongated shaft assembly from rotation of the drive assembly when rotation of the elongated shaft assembly has reached an adjustable predetermined torque setting.

20 Claims, 2 Drawing Sheets

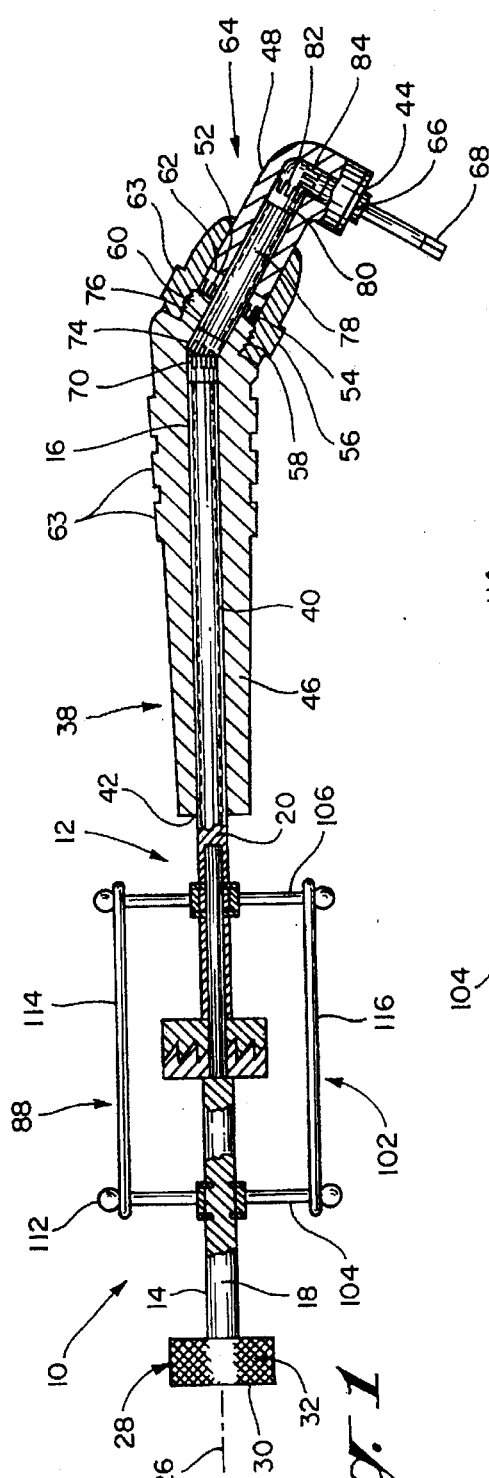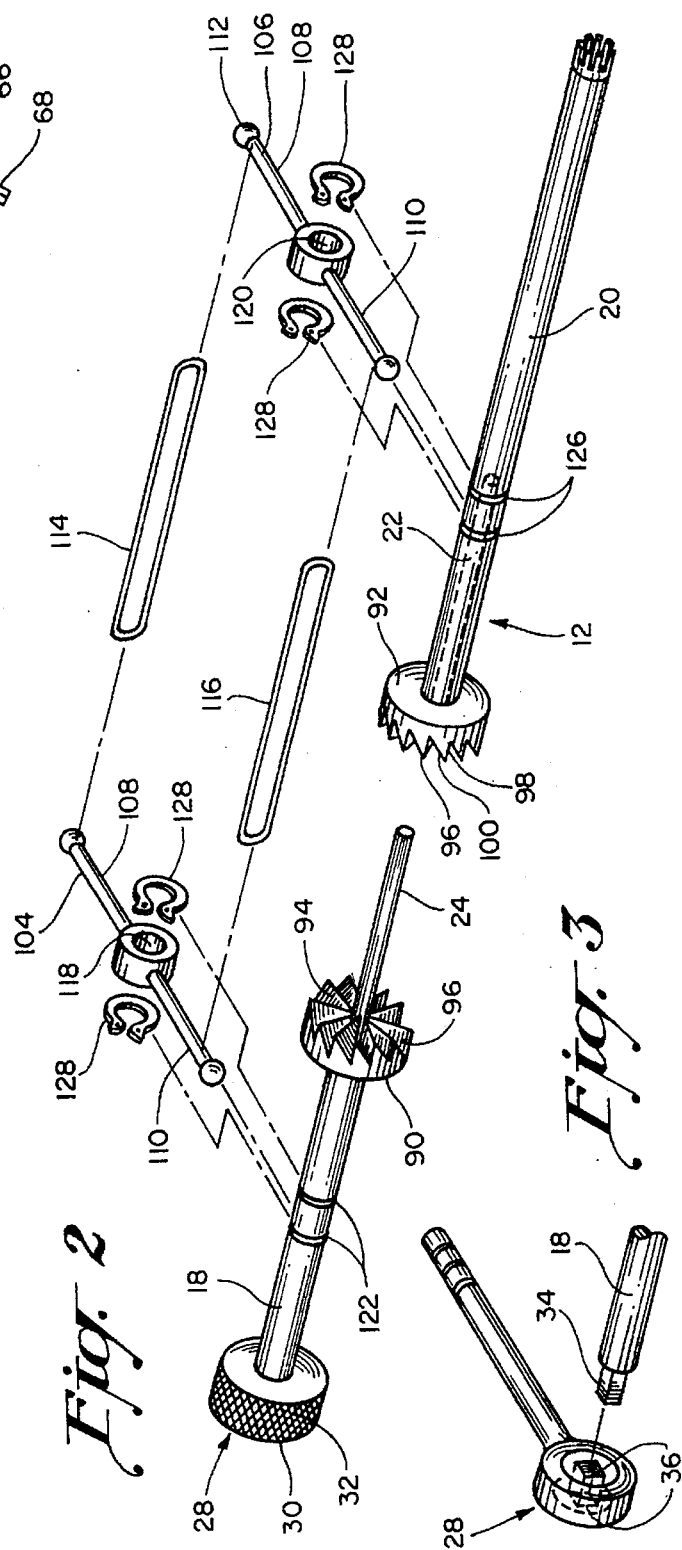

IMPLANT TORQUE WRENCH

BACKGROUND OF THE INVENTION

1. Field of the Invention

The present invention relates generally to torque wrenches for dental components. More particularly, the invention pertains to an improved dental torque wrench having an adjustable torque limiting assembly for use with dental implants.

2. Description of the Prior Art

In dentistry, the installation of dental implants is precision work that involves the use of tiny screws and other components that must be manipulated within a patient's mouth. Due to very limited space and visibility, this work can often become problematic. Great care must be taken by the dentist so that the implants are properly installed and so that screws and other fixtures or hardware are not dropped down the throat of a patient.

Torque wrenches are known to be a useful and important tool in this type of work. The dental implant screws must be engaged at a particular maximum torque setting. Additionally, a proper installation of the dental implant requires a consistency of torque settings for the all of the screws of a particular dental implant. The recommended torque setting will often vary between manufacturers of different implants, so the ability to be able to adjust the maximum torque setting of a wrench would be a desirable feature.

Various prior art torque wrenches devices are known in the art. For example, U.S. Pat. No. 5,295,831 issued to Patterson et al. discloses a dental implant torque wrench constructed of a single shaft of predetermined material and dimension such that application of a predetermined torque to the dental component through the shaft produces a deformity in the shaft to prevent over torquing. While this device serves to provide a satisfactory torque wrench, it suffers from the clear disadvantages of being unadjustable to varied torque settings and being difficult to manipulate in the close quarters of the mouth when each turn of the wrench requires repositioning of the screw bit on the screw or dental component.

U.S. Pat. No. 5,129,823 issued to Hughes discloses a tool for the installation of an abutment or screw in implant dentistry. The tool has a knob manually rotatable on one end of an arm and a bit, releasably secured on a sprocket, rotatable inside the patient's mouth in response to rotation of the knob. Similar to the present invention, the Hughes device can be maintained motionless during installation procedure as the knob is rotated, which is unlike conventional ratcheting mechanisms. However, the Hughes suffers from the distinct disadvantage of being unable to apply a maximum torque setting, which is a critical feature needed in implant dentistry.

U.S. Pat. No. 3,852,884 issued to Lazarus discloses an angle drive manually-operated tool for winding and tightening around a tooth with a pre-formed dental matrix band. The tool having a palm grip rotatably mounted on one end of an elongated rotatable driving member and on its other end a replaceably mounted flexible drive sleeve unit with a pre-angled guide shaft internally and pivotally suspended therein. Unlike Hughes and the present invention, the end of the tool or palm grip of Lazarus remains stationary while it is the elongated rotatable driving member that is manually turned with the fingers. This manner of operation may be satisfactory for use with a dental matrix band, but does not allow for the precision operation involving small screws and components associated with implant dentistry. Furthermore, the Lazarus device does not have a torque limiting means that is adjustable to varied torque settings.

As will be described in greater detail hereinafter, the implant torque wrench of the present invention differs from those previously proposed and employs a number of novel features that render it highly advantageous over the aforementioned prior art.

SUMMARY OF THE INVENTION

Accordingly, it is an object of this invention to provide an implant torque wrench with an adjustable torque limiting assembly that disengages the torquing ability of the wrench when a predetermined torque setting has been reached.

Another object of this invention is to provide an implant torque wrench having an end that is adapted for receiving a tool bit that adjustable into varied angled relationships to provide a wrench that will be positionable to reach dental implant screws in rear most portions of a patient's mouth.

Still another object of this invention is to provide an implant torque wrench that is manually operated while keeping the body of the wrench motionless.

Yet another object of this invention is to provide an implant torque wrench having a torque limiting assembly that is easily adjustable to varied torque settings.

To achieve the foregoing and other objectives, and in accordance with the purposes of the present invention a manually operated dental implant torque wrench is provided. The dental implant torque wrench comprises an elongated shaft assembly having a first shaft end and a second shaft end. A manually operable control device is connected to the first shaft end of the elongated shaft assembly for rotating the elongated shall assembly. An angled housing assembly having a passageway extending from a first open end of the housing to a second open end of the housing is provided. The housing having a first portion and a second portion in an angled relationship to the first portion. A drive assembly is provided within the passageway and is operatively connected to the elongated shaft assembly. The drive assembly includes a receptacle end rotatably mounted to the second open end and adapted for attaching a dental tool thereto. An adjustable torque limiting assembly is connected to the elongated shaft assembly for disengaging the elongated shaft assembly from rotation of the drive assembly when rotation of the elongated shaft assembly has reached an adjustable predetermined torque setting.

In accordance with an aspect of the invention, means connected to the angled housing assembly are provided for adjustably holding the second portion of the angled housing assembly in varied rotational relationship to the first portion.

In accordance with another aspect of the invention, the adjustable torque limiting assembly includes a first gear connected in axial alignment to a first shaft member of the elongated shaft assembly, a second gear connected in axial alignment to a second shaft member of the elongated shaft assembly, the first gear and the second gear each having a set of gear teeth matingly engageable with one another, and tension means for holding the first gear and the second gear in mated engagement for rotation with one another up to a predetermined torque setting.

Other objects, features and advantages of the invention will become more readily apparent upon reference to the following description when taken in conjunction with the accompanying drawings, which drawings illustrate several embodiments of the invention.

BRIEF DESCRIPTION OF THE DRAWINGS

In the drawings:

FIG. 1 is a partial sectional view of the present invention;

FIG. 2 is an exploded perspective view of a preferred embodiment of a torque limiting assembly of the present invention;

FIG. 3 is a perspective view of an alternative embodiment of the control knob of the present invention;

DETAILED DESCRIPTION OF THE PREFERRED EMBODIMENT

Figure 4:
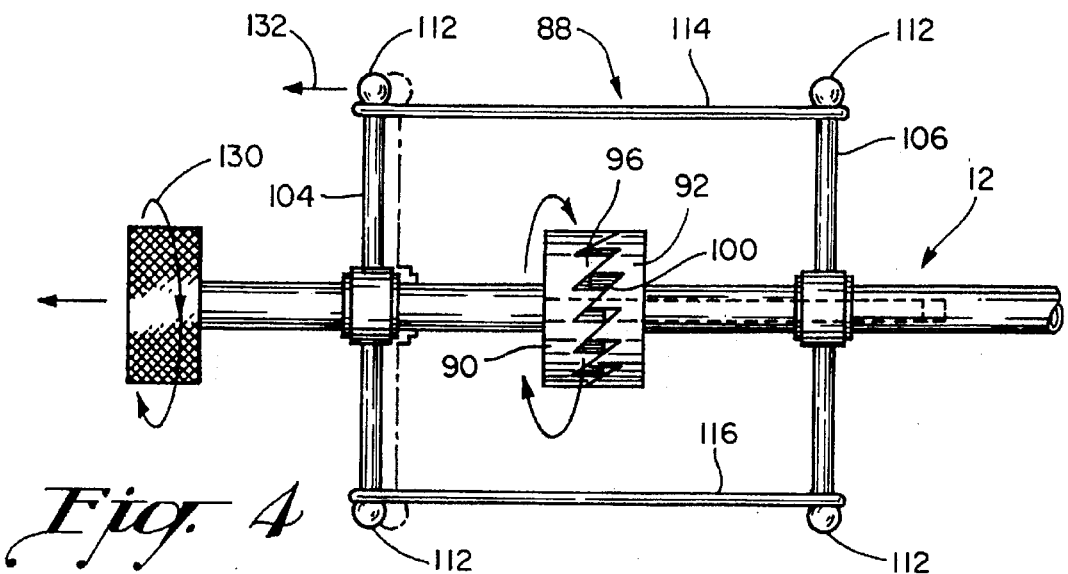
FIG. 4 is a perspective view of the torque limiting assembly of the present invention showing a condition when the assembly has reached a predetermined torque setting and begins to disengage an elongated shaft assembly.

Referring now to the drawings, a manually operated dental implant torque wrench 10 is illustrated in FIG. 1. The wrench 10 has an elongated shaft assembly 12 having a first shaft end 14 and a second shaft end 16. The elongated shaft assembly 12 has a first shaft member 18 and a second shaft member 20 operatively connected to one another. This connection preferably achieved by the second shaft member 20 having a bore 22 and the first shaft member 18 having a shaft extension portion or guide 24 movably engaging the bore 22 of the second shaft member 20 to allow for both rotational movement and for movement along a common longitudinal axis 26.

A manually operable control assembly 28 is connected to the first shaft end 14 of the elongated shaft assembly 12 for rotating the elongated shaft assembly 12. In a preferred embodiment shown in FIGS. 1 and 2, a finger adjustment knob 30 having an outer knurled surface 32 is mounted for manual rotation about a common axis with the first shaft end 14 of the elongated shaft assembly 12. The finger adjustment knob 30 may be mounted for direct rotation of the elongated shaft assembly 12 or a ratcheting mechanism of conventional design could be inserted within the knob 30 to create a ratcheting movement. Alternatively, a ratchet assembly 32 of conventional design may be operatively connected to the first shaft end 14 of the elongated shaft assembly 12, as shown in FIG. 3. Both the ratchet assembly 32 or the knob 30 can be removably mounted by the use of a square peg portion 34 on the first shaft end 14 which engages a mated square bore 36. The additional use of spring loaded ball bearing (not shown) of conventional design mounted on the square peg portion 34 can provide a locking mechanism. The ratchet assembly 32 or knob 30 can alternatively be provided with a square bore 36 on an opposite side, as shown in FIG. 3, to allow for reversibility with respect to connection to the first shaft end 14. This provides a simple and cost effective manner of achieving a forward and reverse direction for ratcheting.

As illustrated in FIG. 1, an angled housing assembly 38 is provided having a passageway 40 extending from a first open end 42 of the housing assembly 38 to a second open end 44 of the housing assembly 38. The housing is formed of a strong lightweight material such as aluminum and has a first portion 46 and a second portion 48 in an angled relationship to the first portion 46. The second portion 48 of the angled housing assembly 38 being sized for placement of a receptacle end 66 in approximate proximity to a rear most portion of a patient's mouth. Preferably, the second portion 48 is angled 90 degrees as shown in FIG. 1. Confronting circumferential edges 52 of the first portion 46 and second portion 48 have square teeth 54 for mated engagement with one another to hold the first portion 46 and second portion 48 in a selected position. A screw member 56 has internal threads 58 for threaded engagement with outer threads 60 of the first portion 46 to pressingly hold an annular flange 62 of the first portion 46 together with the second portion 48. By unscrewing the screw member 56, the second portion 48 of the angled housing assembly 38 can be placed in varied rotational relationship to the first portion 46 to produce a multitude of different angles to reach implant screws at various positions within a patient's mouth. Outer knurled surfaces 63 extend annularly around the housing assembly 38 to provide for improved gripping.

A drive assembly 64 extends within the passageway 40 and is operatively connected to the elongated shaft assembly 12 for transferring rotational forces from the elongated shaft assembly 12 to a receptacle end 66 rotatably mounted to the second open end 44. The receptacle end 66 has a bore adapted for interchangeably attaching a dental tool or bit 68 thereto.

In a preferred embodiment shown in FIG. 1, the second shaft end 16 has a first set of gear teeth 70 along a circumferential edge 72 which engage a second set of gear teeth 74 on a first end 76 of an axle 78. A second end 80 of the axle 78 has a third set of gear teeth 82 which engage a fourth set of gear teeth 84 located on an inner end 86 of the receptacle end 66. It should be understood that other configurations gears or the use of pulleys or sprockets of conventional design for transferring rotational forces could alternatively be used.

An adjustable torque limiting assembly 88 is connected to the elongated shaft assembly 12 for disengaging the elongated shaft assembly 12 from rotation of the drive assembly 64 when rotation of the elongated shaft assembly 12 has reached an adjustable predetermined torque setting. Generally, the torque setting is 32 Newton centimeters. However, manufacturer specifications for implant devices can vary. Most require a setting that would fall in the range of 30 Newton centimeters to 40 Newton centimeters. The adjustable torque limiting assembly 88 is positioned remote from the second open end 44 so that the angle housing assembly 38 can be reduced in size for enabling movement in or around the mouth of a patient.

As best illustrated in FIG. 2, the adjustable torque limiting assembly has a first gear 90 connected in axial alignment to the first shaft member 18 of the elongated shaft assembly 12. A second gear 92 is connected in axial alignment to the second shaft member 20 of the elongated shaft assembly 12. The first gear and the second gear each have a set of gear teeth 94 matingly engageable with one another. Each set of gear teeth 94 includes a plurality of gear tines 96 which are preferably formed in a radially extending configuration so that the gear tines 96 have greater surface area for engagement. Each gear tine 96 has first surface 98 extending in planar parallelism with the longitudinal axis 26 of the elongated shaft assembly 12 and a second surface 100 extending in planar angled relationship with the first surface 98.

A tension assembly 102 is provided for holding confronting surfaces of the first gear 90 and the second gear 92 in mated engagement for rotation with one another up to a predetermined torque setting.

In a preferred embodiment, the tension assembly 102 includes a first tension rod 104 transversely mounted to the first shaft member 18 and is rotatable thereon by having the first shaft member 18 rotatably engage a bore 118 of rod 104. A second tension rod 106 is transversely mounted to the second shaft member 20 and is rotatable thereon by having the second shaft member 20 rotatably engage a bore 120 of rod 106. The first tension rod 104 and second tension rod 106 each have a first rod end 108 and second rod end 110. The first and second rod ends including a spherical retaining end 112. A first elastic band 114 is mounted between first rod ends 108 of the first tension rod 104 and the second tension rod 106. A second elastic band 116 is mounted between second rod ends 110 of the first tension rod 104 and the second tension rod 106.

The first shaft member 18 has a first pair of annular channels 122. A first pair of resilient snap rings or clips 124 engage the first pair of annular channels 122 on either sides of the bore 118 of the first tension rod 104. The second shaft member 20 has a second pair of annular channels 126. A second pair of resilient snap rings or clips 128 engage the second pair of annular channels 126 on either sides of the bore 120 of the second tension rod 106.

The first and second elastic bands are formed of rubber or other elastic material and are selected of suitable size and dimension to produce a desired torque setting. It is to be understood that springs and other biasing or resilient members of known design could be employed.

Figure 6:
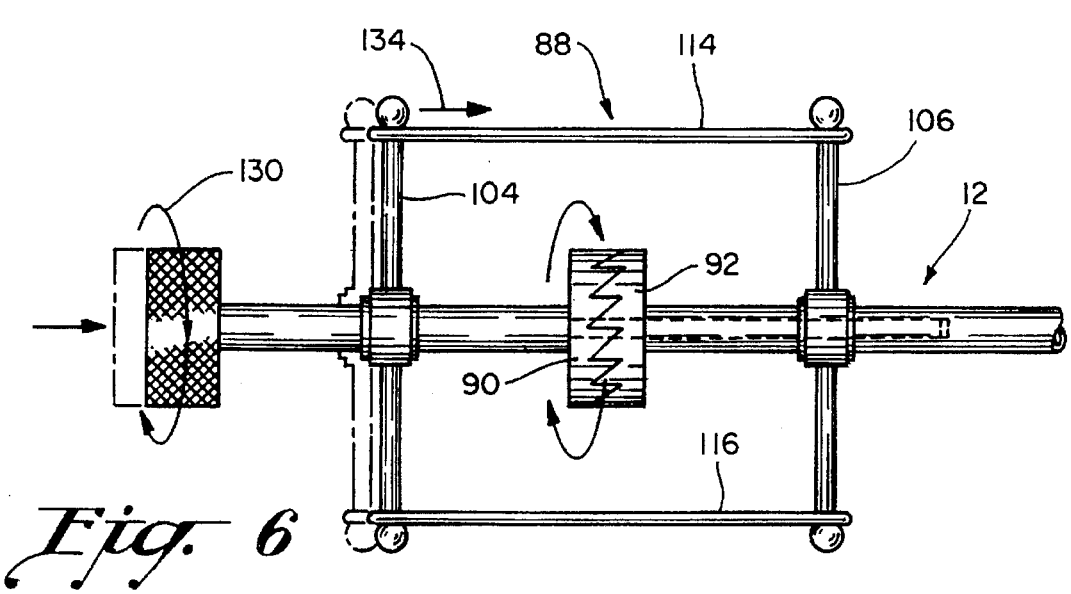
FIG. 6 is a perspective view of the torque limiting assembly of the present invention showing a condition when the assembly has not reached a predetermined torque setting and is engaging the elongated shaft assembly.

In operation, a forward rotation 130, shown in FIG. 6, of the manually operable control assembly 28 shows the first gear 90 and second gear 92 in mated engagement to allow the elongated shaft assembly to supply rotational forces through the drive assembly 64 to turn bit 68.

FIG. 4 shows a forward rotation 130 where the bit 68 has reached a predetermined torque setting. The first gear 90 and second gear 92 begin to disengage by confronting second surfaces 100 of each gear tine 96 pushing against one another due to a force 132 caused by continued rotation of the control assembly 28 that pulls the first tension rod 104 in a direction away from the second tension rod 106. The force 132 must be greater than the force created by the first elastic band 114 and the second elastic band 116 which are pulling to hold the first gear 90 and second gear 92. It should be understood that because each gear tine has first surface 98 which is in planar parallelism with the longitudinal axis 26, a reverse direction opposite the forward rotation 130 will allow the first surfaces 98 to engage. Therefore, the torque limiting ability will only be in operation during forward rotation 130. While producing first surfaces 98 that are angled would allow for torque limiting ability, it is considered advantageous to only operate this feature when a dentist would be screwing in a screw or other component.

Figure 5:
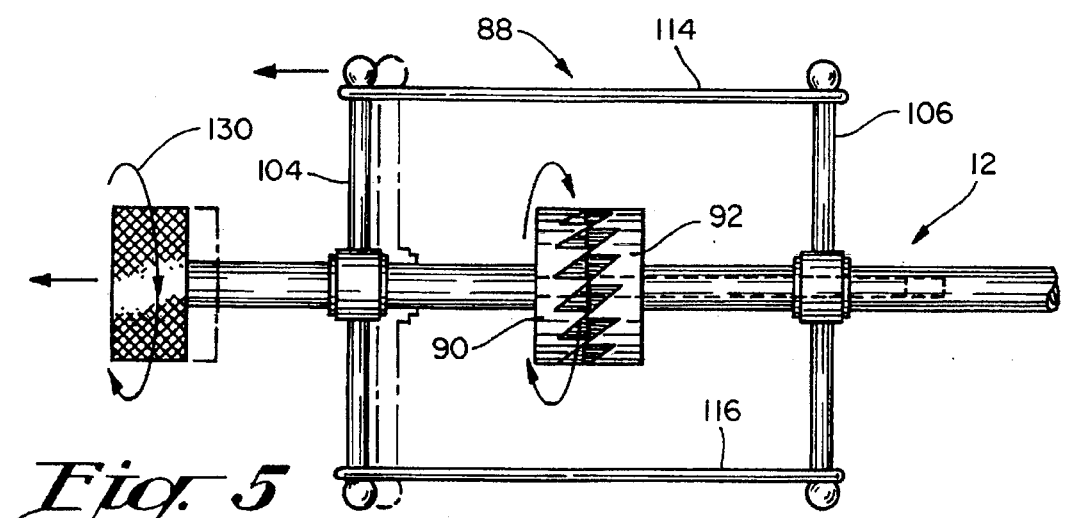
FIG. 5 is a perspective view of the torque limiting assembly of the present invention showing a condition when the assembly has reached a predetermined torque setting and has completely disengaged the elongated shaft assembly.

FIG. 5 shows a forward rotation 130 where the bit 68 has continued to maintain a torque greater that the maximum torque setting. The second gear 92 continues to remain still while the first gear 90 rotates against it with the confronting sets of gear teeth 94 being disengaged. Referring now to FIG. 6, a force 134 created by the contracting first elastic band 114 and the second elastic band 116, which is less than the force 132 pulls the first gear 90 and second gear 92 back into engagement. A clamp of common design (not shown) can be connected between the first and second gears or between the first and second tension rods to hold the first and second gears in constant engagement when the torque limiting feature is not desired.

The maximum torque setting can be easily adjusted by simply replacing the first and second elastic bands with elastic bands having stronger or weaker contracting forces that will produce the desired torque setting. Furthermore, calibration of the wrench 10 is not needed since replacement of the elastic bands will create the desired torque. Replacement of the elastic bands for each dental implant installation would inexpensively assure the dentist of the accuracy of the wrench 10.

Although the invention has been described by reference to some embodiments it is not intended that the novel device be limited thereby, but that modifications thereof are intended to be included as falling within the broad scope and spirit of the foregoing disclosure, the following claims and the appended drawings.

We claim:

1. A manually operated dental implant torque wrench comprising:

(a) an elongated shaft assembly having a first shaft end and a second shaft end, the elongated shaft assembly having a first shaft member and a second shaft member, the second shaft member having a bore, the first shaft member having a shaft extension portion movably engaging the bore of the second shaft member;

(b) manually operable control means connected to the first shaft end of the elongated shaft assembly for rotating the elongated shaft assembly;

(c) an angled housing assembly having a passageway extending from a first open end of the angled housing assembly to a second open end of the angled housing assembly, the angled housing assembly having a first portion and a second portion in an angled relationship to the first portion;

(d) drive means extending within the passageway and operatively connected to the elongated shaft assembly for transferring rotational forces from the elongated shaft assembly to a receptacle end rotatably mounted to the second open end, the receptacle end being adapted for attaching a dental tool thereto; and (e) adjustable torque limiting means connected to the elongated shaft assembly for disengaging the elongated shaft assembly from rotation of the drive means when rotation of the elongated shaft assembly has reached an adjustable predetermined torque setting, the adjustable torque limiting means being positioned remote from the second open end of the angled housing assembly, the adjustable torque limiting means including a first gear connected in axial alignment to the first shaft member of the elongated shaft assembly, a second gear connected in axial alignment to the second shaft member of the elongated shaft assembly, the first gear and the second gear each having a set of gear teeth matingly engageable with one another, and tension means for holding the first gear and the second gear in mated engagement for rotation with one another up to a predetermined torque setting.

2. The dental implant torque wrench of claim 1, further comprising means connected to the angled housing assembly for adjustably holding the second portion of the angled housing assembly in varied rotational relationship to the first portion.

3. The dental implant torque wrench of claim 1, wherein the manually operable control means includes a finger adjustment knob connected to and in axial alignment with the first shaft end of the elongated shaft assembly.

4. The dental implant torque wrench of claim 1, wherein the manually operable control means includes a ratchet assembly operatively connected to the first shaft end of the elongated shaft assembly.

5. The dental implant torque wrench of claim 1, wherein the tension means includes a first tension rod transversely mounted to the first shaft member and being rotatable thereon, a second tension rod transversely mounted to the second shaft member and being rotatable thereon, the first tension rod and second tension rod each having a first rod end and second rod end, a first elastic band mounted between first rod ends of the first tension rod and the second tension rod, and a second elastic band mounted between second rod ends of the first tension rod and the second tension rod.

6. The dental implant torque wrench of claim 5, further comprising the first shaft member having a first pair of annular channels, a first pair of clips engaging the first pair of annular channels on either sides of the first tension rod, the second shaft member having a second pair of annular channels, a second pair of clips engaging the second pair of annular channels on either sides of the second tension rod.

7. A manually operated dental implant torque wrench for screwing dental implant components to an adjustable torque setting, comprising:

(a) an elongated shaft assembly having a first shaft end and a second shaft end;

(b) manually operable control means connected to the first shaft end of the elongated shaft assembly for rotating the elongated shaft assembly;

(c) an angled housing assembly having a passageway extending from a first open end of the angled housing assembly to a second open end of the angled housing assembly, the angled housing assembly having a first portion and a second portion in an angled relationship to the first portion;

(d) drive means extending within the passageway and operatively connected to the elongated shaft assembly for transferring rotational forces from the elongated shaft assembly to a receptacle end rotatably mounted to the second open end, the receptacle end being adapted for attaching a dental tool thereto; and (e) means connected to the elongated shaft assembly for disengaging the elongated shaft assembly from rotation of the drive means when rotation of the elongated shaft assembly has reached an adjustable predetermined torque setting, said means being positioned remote from the second open end of the angled housing assembly.

8. The dental implant torque wrench of claim 7, further comprising means connected to the angled housing assembly for adjustably holding the second portion of the angled housing assembly in varied rotational relationship to the first portion.

9. The dental implant torque wrench of claim 7, wherein the manually operable control means includes a finger adjustment knob connected to and in axial alignment with the first shaft end of the elongated shaft assembly.

10. The dental implant torque wrench of claim 7, wherein the manually operable control means includes a ratchet assembly operatively connected to the first shaft end of the elongated shaft assembly.

11. The dental implant torque wrench of claim 7, wherein the elongated shaft assembly further comprises a first shaft member and a second shaft member, the second shaft member having a bore, the first shaft member having a shaft extension portion movably engaging the bore of the second shaft.

12. The dental implant torque wrench of claim 11, wherein the means connected to the elongated shaft assembly includes a first gear connected in axial alignment to the first shaft member of the elongated shaft assembly, a second gear connected in axial alignment to the second shaft member of the elongated shaft assembly, the first gear and the second gear each having a set of gear teeth matingly engageable with one another, and tension means for holding the first gear and the second gear in mated engagement for rotation with one another up to a predetermined torque setting.

13. The dental implant torque wrench of claim 12, wherein the tension means includes a first tension rod transversely mounted to the first shaft member and being rotatable thereon, a second tension rod transversely mounted to the second shaft member and being rotatable thereon, the first tension rod and second tension rod each having a first rod end and second rod end, a first elastic band mounted between first rod ends of the first tension rod and the second tension rod, and a second elastic band mounted between second rod ends of the first tension rod and the second tension rod.

14. The dental implant torque wrench of claim 13, further comprising the first shaft member having a first pair of annular channels, a first pair of clips engaging the first pair of annular channels on either sides of the first tension rod, the second shaft member having a second pair of annular channels, a second pair of clips engaging the second pair of annular channels on either sides of the second tension rod.

15. The dental implant torque wrench of claim 12, wherein each set of gear teeth includes a plurality of gear tines, each gear tine having first surface extending in planar parallelism with a longitudinal axis of the elongated shaft assembly and a second surface extending in planar angled relationship with the first surface.

16. The dental implant torque wrench of claim 15, wherein the plurality of gear tines are formed in a radially extending configuration.

17. The dental implant torque wrench of claim 16, wherein the second portion of the angled housing assembly being sized for placement of the receptacle end in approximate proximity to a rear most portion of a patient's mouth.

18. A manually operated dental implant torque wrench comprising in combination:

(a) an elongated shaft assembly having a first shaft end and a second shaft end, the elongated shaft assembly having a first shaft member and a second shaft member operatively connected to one another;

(b) manually operable control means connected to the first shaft end of the elongated shaft assembly for rotating the elongated shaft assembly;

(c) an angled housing assembly having a passageway extending from a first open end of the angled housing assembly to a second open end of the angled housing assembly, the angled housing assembly having a first portion and a second portion in an angled relationship to the first portion, the second portion of the angled housing assembly being sized for placement of a receptacle end in approximate proximity to a rear most portion of a patient's mouth, and means connected to the angled housing assembly for adjustably holding the second portion of the angled housing assembly in varied rotational relationship to the first portion;

(d) drive means extending within the passageway and operatively connected to the elongated shaft assembly for transferring rotational forces from the elongated shaft assembly to the receptacle end rotatably mounted to the second open end, the receptacle end being adapted for attaching a dental tool thereto; and (e) adjustable torque limiting means connected to the elongated shaft assembly for disengaging the elongated shaft assembly from rotation of the drive means when rotation of the elongated shaft assembly has reached an adjustable predetermined torque setting, the adjustable torque limiting means being positioned remote from the second open end of the angled housing assembly, the adjustable torque limiting means including a first gear connected in axial alignment to the first shaft member of the elongated shaft assembly, a second gear connected in axial alignment to the second shaft member of the elongated shaft assembly, the first gear and the second gear each having a set of gear teeth matingly engageable with one another, and tension means for holding the first gear and the second gear in mated engagement for rotation with one another up to a predetermined torque setting.

19. The dental implant torque wrench of claim 18, wherein the tension means includes a first tension rod transversely mounted to the first shaft member and being rotatable thereon, a second tension rod transversely mounted to the second shaft member and being rotatable thereon, the first tension rod and second tension rod each having a first rod end and second rod end, a first elastic band mounted between first rod ends of the first tension rod and the second tension rod, and a second elastic band mounted between second rod ends of the first tension rod and the second tension rod.

20. The dental implant torque wrench of claim 19, wherein each set of gear teeth includes a plurality of gear tines, each gear tine having first surface extending in planar parallelism with a longitudinal axis of the elongated shaft assembly and a second surface extending in planar angled relationship with the first surface.

* * * * *